(12) United States Patent
Emberger et al.

(10) Patent No.: US 9,920,696 B2
(45) Date of Patent: Mar. 20, 2018

(54) METHOD FOR OPERATING A GAS TURBINE AND GAS TURBINE UNIT USEFUL FOR CARRYING OUT THE METHOD

(75) Inventors: Norbert Walter Emberger, Neuenhof (CH); Pankaj Bajaj, Zürich (CH); Michael Kenyon, Baden (CH); Frank Keppler, Wangen b. Olten (CH); Tobias Christian Amsler, Murg (DE); Mengbin Zhang, Otelfingen (CH); Zlatko Pavlic, Nussbaumen (CH)

(73) Assignee: ANSALDO ENERGIA IP UK LIMITED, London (GB)

( * ) Notice: Subject to any disclaimer, the term of this patent is extended or adjusted under 35 U.S.C. 154(b) by 105 days.

(21) Appl. No.: 13/555,331

(22) Filed: Jul. 23, 2012

(65) Prior Publication Data
US 2013/0036744 A1     Feb. 14, 2013

(30) Foreign Application Priority Data

Aug. 9, 2011   (CH) ...................................... 1313/11

(51) Int. Cl.
*F02C 9/40*     (2006.01)
*F02C 9/34*     (2006.01)
(Continued)

(52) U.S. Cl.
CPC .................. *F02C 9/40* (2013.01); *F02C 9/28* (2013.01); *F02C 9/34* (2013.01); *F02C 9/48* (2013.01);
(Continued)

(58) Field of Classification Search
USPC ... 60/39.24, 39.26, 39.27, 39.281, 233, 243, 60/790, 793
See application file for complete search history.

(56) References Cited

U.S. PATENT DOCUMENTS 4,201,923 A * 5/1980 Reed et al. .................. 290/40 R
6,813,875 B2 * 11/2004 Inoue ........................ F02C 3/22
                                            60/39.281
(Continued)

FOREIGN PATENT DOCUMENTS

CN          1623031 A      6/2005
DE         10308384        9/2004
(Continued)

OTHER PUBLICATIONS

Search Report for Swiss Patent App. No. 01313/11 (dated Mar. 28, 2012).
(Continued)

*Primary Examiner* — Gerald L Sung
*Assistant Examiner* — Scott Walthour
(74) *Attorney, Agent, or Firm* — Buchanan Ingersoll & Rooney PC

(57) ABSTRACT

A method for operating a gas turbine (11) having a compressor (12), a turbine (14) and a combustor (13) with a pilot burner group (15a), a rich premix burner group (15b) and a lean premix burner group (15c), under changing composition of the incoming fuel gas (16), includes the steps of: continuously measuring, in real time, the composition of the fuel gas (16); and controlling the operation of the gas turbine (11) and the combustion of the burners (15a-c) by using the real time fuel gas composition measurements.

17 Claims, 2 Drawing Sheets

(51) Int. Cl.
*F02C 9/28* (2006.01)
*F02C 9/48* (2006.01)
*G01N 21/3504* (2014.01)

(52) U.S. Cl.
CPC . *F05B 2270/15* (2013.01); *F23R 2900/00013* (2013.01); *G01N 21/3504* (2013.01)

(56) References Cited

U.S. PATENT DOCUMENTS

| | | | |
|---|---|---|---|
| 7,216,486 B2 | 5/2007 | Doebbeling et al. | |
| 7,516,608 B2 | 4/2009 | Hellat et al. | |
| 2004/0011050 A1* | 1/2004 | Inoue | F02C 3/22 60/773 |
| 2004/0226297 A1* | 11/2004 | Griffin | F23C 7/002 60/737 |
| 2005/0028530 A1* | 2/2005 | Doebbeling et al. | 60/773 |
| 2006/0174630 A1* | 8/2006 | Hellat | F02C 9/28 60/776 |
| 2007/0082306 A1* | 4/2007 | Drnevich | C10J 3/00 431/12 |
| 2007/0119178 A1* | 5/2007 | Berenbrink et al. | 60/773 |
| 2008/0115482 A1* | 5/2008 | LaGrow et al. | 60/39.281 |
| 2010/0205976 A1* | 8/2010 | Nag et al. | 60/775 |
| 2010/0286890 A1* | 11/2010 | Chandler | 701/100 |
| 2012/0036863 A1* | 2/2012 | Kirzhner et al. | 60/776 |
| 2012/0102967 A1* | 5/2012 | Kirzhner et al. | 60/773 |

FOREIGN PATENT DOCUMENTS

| | | |
|---|---|---|
| EA | 008575 | 6/2007 |
| EP | 1211498 | 6/2002 |
| RU | 2 146 769 | 3/2000 |
| RU | 2 249 152 C1 | 3/2005 |
| SU | 240391 | 1/1983 |
| WO | WO03/062618 | 7/2003 |
| WO | WO2008/144372 | 11/2008 |

OTHER PUBLICATIONS

Office Action dated Jun. 5, 2014, by the Russian Patent Office in corresponding Russian Patent Application No. 2012134070, and an English Translation of the Office Action. (10 pages).

Apr. 3, 2015 Russian Office Action issued in Russian Application No. 2012134070 (with English language translation).

Nov. 29, 2016 Notice of Reexamination issued by SIPO in Chinese Application No. 201210279929.3 (with English language translation).

* cited by examiner

METHOD FOR OPERATING A GAS TURBINE AND GAS TURBINE UNIT USEFUL FOR CARRYING OUT THE METHOD

This application claims priority under 35 U.S.C. § 119 to Swiss App. No. 01313/11, filed 9 Aug. 2011, the entirety of which is incorporated by reference herein.

BACKGROUND

Field of Endeavor

The present invention relates to the technology of gas turbines. It refers to a method for operating a gas turbine, and in particular to a method for reliable operation of a gas turbine in changing fuel gas compositions. It further relates to a gas turbine unit useful for carrying out the method.

Brief Description of the Related Art

Usually gas turbines are fuelled with natural gas. Natural gas is mainly composed of $CH_4$ (methane). Furthermore, natural gas also contains so-called non-$CH_4$ components that can be diluting or enrichment substances. Examples of diluting substances are $N_2$ (nitrogen) and $CO_2$ (carbon dioxide). Enrichment substances usually are higher saturated hydrocarbons ($C_{2+}$) such as $C_2H_6$ (ethane), $C_3H_8$ (propane), butane, etc.

Currently it is customary to characterize the quality, i.e., the composition of natural gas, by using two indices. These are the calorific value on one hand and the Wobbe index on the other hand. Up until now it furthermore has been customary to operate gas turbines with natural gas of consistent quality. Today gas supply companies are not yet able to guarantee consistent quality for the natural gas they supply.

As part of the liberalization of the natural gas market, natural gas suppliers increasingly attempt to optimize natural gas demand and natural gas prices. The result is that natural gas is obtained from different sources, is mixed and supplied to the consumers. This in turn results in a high degree of variability of the natural gas with regard to quality and/or composition.

It is clear that these varying properties of the natural gas influence the combustion process in the gas turbine combustor and consequently significantly influence the gas turbine operation. A change in fuel gas drives the gas turbine outside of its optimal operation window. This has an impact on the emission and pulsation behaviour and reduces the operational reliability. Therefore, power plant operators must be prepared for varying natural gas quality in the future.

It has already been proposed in the past (see, for example, U.S. Pat. Nos. 7,216,486 and 7,516,608) to measure the $C_{2+}$ alkane content of the fuel gas and change the distribution of the fuel mass flows between the various combustion chambers and burners in accordance with variations of the fuel gas composition. An adjustment of the gas turbine operating parameters based on the rate of change in fuel gas energy content is disclosed in U.S. Pat. No. 7,854,110.

On the other hand, it has been proposed (see, for example, U.S. Pat. No. 7,484,352, and U.S. Pat. App. Pub. Nos. 2006/0040225 and U.S. 2009/0037029) to change the distribution of the fuel mass flows between the various combustion chambers and burners in dependence of pulsations being excited in the combustion chamber.

However, there is still a need for a better adaptation of the gas turbine operation to fast changing fuel gas compositions to improve the operational stability and reliability of a gas turbine.

SUMMARY

One of numerous aspects of the present invention includes ensuring that, even with a wide range of fast changing fuel gas compositions, the gas turbine always is running in its optimum operation window.

Another aspect includes providing optimum emission and pulsation behaviour as well as operational reliability of the gas turbine.

Yet another aspect includes a method for operating a gas turbine, the gas turbine including a compressor, a turbine and a combustor with a pilot burner group, a rich premix burner group and a lean premix burner group, under changing composition of the incoming fuel gas, the method comprising the steps of:

Continuously measuring in real time the composition of the fuel gas; and controlling the operation of said gas turbine and the combustion of said burners by using said real time fuel gas composition measurements.

According to an embodiment, the fuel distribution between the pilot burner group, the rich premix burner group and the lean premix burner group is optimized depending on the measured actual fuel gas composition.

According to another embodiment, the composition-dependent combustion control is combined with a pulsation dependent combustion control.

According to a further embodiment, the lower heating value (LHV) and the molecular weight ($M_R$) of the fuel gas are updated online for improved engine control stability during transient engine operation.

According to another embodiment, the fuel gas composition is measured by fast infrared gas analysers (FIRGAs).

According to another embodiment, the total concentration of hydrocarbons with two or more carbon-atoms (C2+) is measured and used as input for the gas turbine control.

According to a further embodiment, in addition the concentrations of $CH_4$, $C_2H_6$, $C_3H_8$ and $CO_2$ are used as input for the gas turbine control.

In a further embodiment, a closed loop control, based on combustor pulsation measurement, is combined with an open loop control, based on the actual fuel gas composition.

Another embodiment includes that the lower heating value (LHV) and the molecular weight ($M_R$) of the gas fuel are estimated by online measuring of the $CH_4$-, $C_2H_6$-, $C_3H_8$- and $CO_2$-concentrations.

A further embodiment includes that a fuel mixing device is arranged upstream of the combustor.

Another aspect includes a gas turbine unit which has a gas turbine comprising a compressor, a turbine and a combustor with a pilot burner group, a rich premix burner group and a lean premix burner group, which burner groups are supplied with a fuel gas under control of a gas turbine control system. Means are provided for analysing the composition of the fuel gas, and the output of said analysing means is connected to said gas turbine control system by an analyser input line.

An embodiment of the gas turbine unit is characterized in that a control valve is provided for each of said burner groups, and said control valves are controlled via a command line by said gas turbine control system.

According to another embodiment of the gas turbine unit, a combustion pulsation monitoring and filtering system monitors said combustor and is connected to said gas turbine control system by a monitoring input line.

In another embodiment of the gas turbine unit, a fuel mixing device is provided upstream of the combustor.

BRIEF DESCRIPTION OF THE DRAWINGS

The present invention is now to be explained more closely by means of different embodiments and with reference to the attached drawings.

DETAILED DESCRIPTION OF EXEMPLARY EMBODIMENTS

Increasing demands are being placed on today's global gas turbine fleet to burn natural gas with higher $C_{2+}$ (higher order hydrocarbons) contents and also with greater, more rapid fluctuations in the $C_{2+}$ content. The present disclosure provides a new control concept for operating a gas turbine that above all would allow accommodating fast changing fuel gas qualities.

The present disclosure is based on the general idea of a control concept using two fast infrared gas analysers (FIRGAs) to detect changing $C_{2+}$ and inert gas contents in the fuel.

Figure 3:
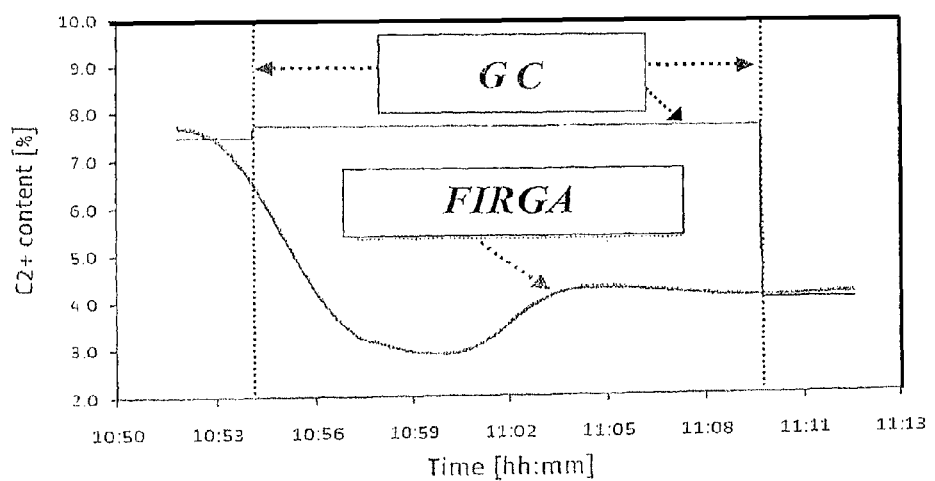
FIG. 3 shows, in an exemplary graph, the principle of fast response (in comparison to gas chromatographs (GCs)) to changes in gas composition, based on fast infrared gas analysers (FIRGAs) in accordance with the invention.

Whereas traditional gas chromatographs (GCs) have response times in the order of five to 20 minutes (see FIG. 3), fast infrared sensors (FIRGAs) have a response time of less than 20 seconds. Methods and systems described herein use this advantageous feature of infrared analysers for the development of a near real time re-optimisation of the operating concept for the current fuel composition.

Figure 1:
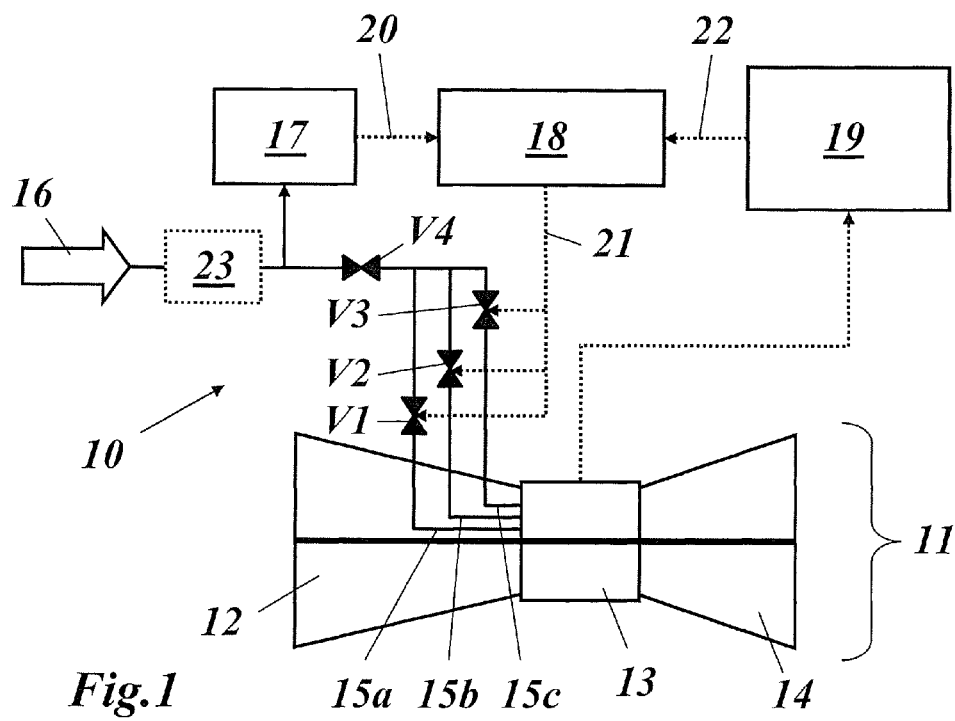
FIG. 1 shows a schematic diagram of a gas turbine unit according to an embodiment of the invention having fast infrared gas analysers and a special gas turbine control system.

FIG. 1 shows a schematic diagram of a gas turbine unit according to an embodiment of the invention having fast infrared gas analysers and a special gas turbine control system. The gas turbine unit 10 includes a gas turbine 11 with a compressor 12, a combustor 13 and a turbine 14. The combustor 13 has three different burner groups 15a-c, i.e., a pilot burner group 15a, a rich premix burner group 15b, and the lean premix burner group 15c. Each burner group is supplied with fuel gas 16, whereby the mass flow of fuel gas is controlled by associated valves V1, V2 and V3. A shut-off valve V4 is provided to interrupt the total fuel gas supply.

The composition of the incoming fuel gas 16 is analysed in real time by fast infrared gas analysers 17, which are connected to a gas turbine control system 18 with an analyser input line 20.

Furthermore, a combustion pulsation monitoring and filtering system 19 is used to monitor the combustor 13 and feed the gas turbine control system 18 with respective data via monitoring input line 22.

The gas turbine control system controls the valves V1, V2 and V3 via command line 21 in accordance with the measurement results of the FIRGAs 17 and the monitoring and filtering system 19.

In addition, a fuel mixing device 23 may be provided upstream of the combustor 13.

Figure 2:
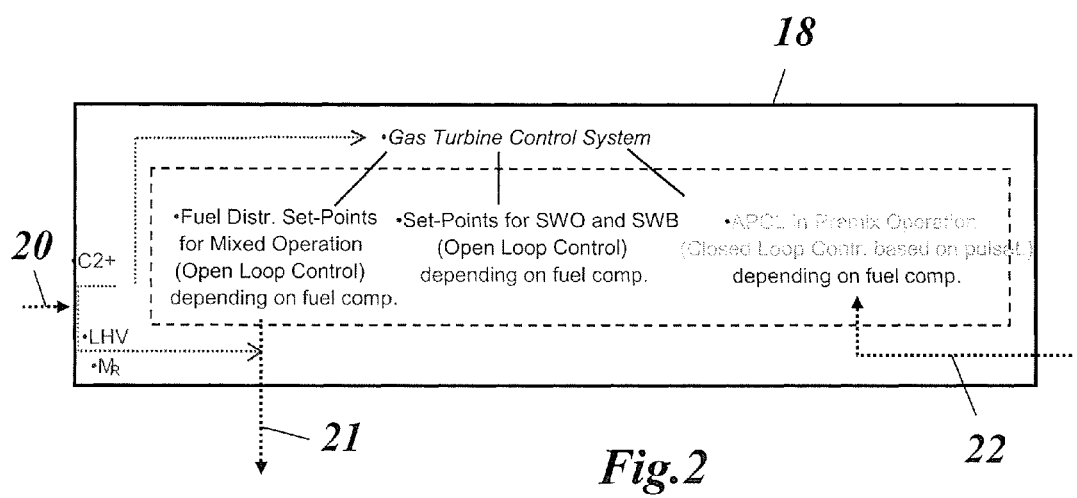
FIG. 2 shows details of the gas turbine control system of FIG. 1.

As FIG. 2 shows, the $C_{2+}$ content directly enters the gas turbine control system. The fuel distribution set points for mixed operation (open loop control) are set depending on the fuel composition. The actual LHV and $M_R$ values are used to improve engine stability. The switch-over (SWO) and switch-back (SWB) set-points (in open loop control) are set depending on the fuel composition. The advanced pulsation control logic (APCL) also depends (in a closed loop control based on pulsations) on fuel composition.

Method for operating a gas turbine according to principles of the present invention may thus include the following basic features:

Control of gas turbine operation and burner combustion by using real time fuel gas concentration measurements, wherein the fuel gas concentration is measured by fast infrared gas analyzers (FIRGAs) 17;

online optimization of the fuel distribution between the pilot burner group 15a, the rich premix burner group 15b, and the lean premix burner group 15c, depending on the actual fuel composition;

combination of the composition based (i.e., $C_{2+}$-dependent) combustion control and the pulsation dependent combustion control; and in addition, an online update of the Lower Heating Value [LHV in MJ/kg] and the molecular weight [$M_R$ in g/mol] for improved engine control stability with transient engine operation.

This concept allows optimized combustion and improved engine reliability with changing fuel gas sources over the whole load range up to base load. The fuel gas mass flow is thereby a function of the relative load RL, the combustion pulsations CP, and the fuel composition FC:

$$\dot{m}_f = f(\text{RL},\text{CP},\text{FC}).$$

For the premix operation range above a switch-over point, combustion pulsation-dependent control with an advanced pulsation control logic is combined with fuel composition-based control to further improve operational reliability with optimized emission and pulsation behavior, even for changing fuel gas sources.

According to an exemplary embodiment, the operation of a gas turbine is characterized by the following features:

Fast infrared gas analyzers (FIRGAs) for real-time measurement of the fuel gas composition are used.

As input for gas turbine control (18), the total concentration of hydrocarbons with two or more carbon-atoms ($C_{2+}$ content) as well as the concentrations of $CH_4$, $C_2H_6$, $C_3H_8$ and $CO_2$ are used.

Optimization of fuel distribution in the premix operation between rich and lean premix burner groups 15b, 15c depending on $C_{2+}$ content.

Combination of a closed loop control, based on combustor pulsation measurement (Advanced Pulsation Control Logic) with an open loop control, based on the actual fuel gas composition.

Tune Switch-Over as well as Switch-Back between piloted and premix fuel gas operation, depending on the measured $C_{2+}$ content.

Optimization of fuel distribution in mixed operation between pilot respectively rich and lean premix burner groups 15a-c.

Online estimation of the Lower Heating Value (LHV) and the Molecular Weight ($M_R$) of Natural Gases and applying this information continuously for an improved transient gas turbine control.

According to an alternative embodiment, the estimation of LHV and $M_R$ of the natural gas based fuels is made without analyzing the gas composition completely, i.e., only the $CH_4$-, $C_2H_6$- $C_3H_8$- and $CO_2$-concentrations are measured online.

In case the $C_{2+}$ content in the fuel gas exceeds certain operational limits, protecting measures for the gas turbine become operative.

The arrangement of a gas fuel mixing device 23 for mixing different kinds of fuel gases upstream of the combustor 13 can reduce very fast gradients in fuel gas properties. This measure additionally ensures stable engine control.

Several advantages of the methods and systems include:
The gas turbine is able now to respond rapidly and reliably to changing fuel gas compositions—even with a wide range of fast changing fuel gas compositions.
The consequences are an improved operation due to real-time optimized engine operation over the entire range of $C_{2+}$ contents of the fuel and a reliable operation due to improved engine reliability with fluctuating $C_{2+}$ contents over the whole range.
Gas turbine operation with the optimum emission and pulsation behavior is ensured. This increases the flexibility of the operator of the gas turbine plant and may put him in a position to take advantage of favorable commercial conditions for changing $C_{2+}$ fuels on the spot market.

LIST OF REFERENCE NUMERALS

10 gas turbine unit
11 gas turbine
12 compressor
13 combustor
14 turbine
15*a,b,c* burner group
16 fuel gas
17 FIRGA
18 gas turbine control system
19 combustion pulsation monitoring and filtering system
20 analyzer input line
21 command line
22 monitoring input line
23 fuel mixing device
GC gas chromatograph
FIRGA fast infrared gas analyser
V1, . . . ,V4 valve While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

We claim:

1. A method for operating a gas turbine unit, the gas turbine unit comprising (i) a gas turbine including a compressor, a turbine, and a combustor with a pilot burner group, a rich premix burner group, and a lean premix burner group, (ii) a gas turbine control system configured and arranged to supply each of the pilot burner group, the rich premix burner group, and the lean premix burner group with a fuel gas, the gas turbine control system comprising an analyzer input line, (iii) a fast infrared gas analyzer configured and arranged to detect changing $C_{2+}$ of the fuel gas, the fast infrared gas analyzer having an output connected to said analyzer input line, and (iv) a combustion pulsation monitoring and filtering system configured and arranged to monitor pulsations of said combustor, the method comprising:
continuously detecting, in real time, changing $C_{2+}$ of the fuel gas using the fast infrared gas analyzer;
controlling switching between a piloted fuel gas operation and a premixed fuel gas operation depending on the detected $C_{2+}$ of the fuel gas, using the gas turbine control system; and
controlling, during the premixed fuel gas operation, operation of said gas turbine and the pilot burner group, the rich premix burner group, and the lean premix burner group, using the gas turbine control system, based on the detected $C_{2+}$ of the fuel gas and the pulsations of the combustor monitored by the combustion pulsation monitoring and filtering system; and
setting a switch over set-point, in the gas turbine control system, for switching over from the piloted fuel gas operation to the premixed fuel gas operation and setting a switch back set-point, in the gas turbine control system, for switching back to the piloted fuel gas operation from the premixed fuel gas operation depending on the detected $C_{2+}$ of the fuel gas, wherein the switch over set-point is a different set-point than the switch back set-point.

2. The method as claimed in claim 1, wherein controlling, during the premixed fuel gas operation, operation of said gas turbine and the pilot burner group, the rich premix burner group, and the lean premix burner group further comprises optimizing a distribution of the fuel gas between the rich premix burner group and the lean premix burner group depending on the detected $C_{2+}$ of the fuel gas.

3. The method as claimed in claim 1, wherein a lower heating value (LHV) and a molecular weight ($M_R$) of the fuel gas are determined for improved gas turbine control stability during transient gas turbine operation.

4. The method as claimed in claim 1, further comprising measuring concentrations of $CH_4$, $C_2H_6$, $C_3H_8$ and $CO_2$ in the fuel gas, and wherein the controlling, during the premixed fuel gas operation, operation of said gas turbine and the pilot burner group, the rich premix burner group, and the lean premix burner group is further based on the measured concentrations of $CH_4$, $C_2H_6$, $C_3H_8$ and $CO_2$ in the fuel gas.

5. The method as claimed in claim 1, wherein controlling, during the premixed fuel gas operation, operation of said gas turbine and the pilot burner group, the rich premix burner group, and the lean premix burner group further comprises controlling with a closed loop control, based on the pulsations of the combustor monitored by the combustion pulsation monitoring and filtering system, and controlling with an open loop control, based on the detected $C_{2+}$ of the fuel gas.

6. The method as claimed in claim 3, wherein determining the LHV comprises estimating the LHV and wherein determining the $M_R$ comprises estimating the $M_R$, and wherein estimating the LHV and estimating the $M_R$ are based on measurements of $CH_4$, $C_2H_6$, $C_3H_8$, and $CO_2$, concentrations in the fuel gas.

7. The method as claimed in claim 1, wherein a fuel mixing device is arranged upstream of the combustor, with respect to a direction of flow of the fuel gas.

8. A gas turbine unit comprising:
a gas turbine having a compressor, a turbine, and a combustor with a pilot burner group, a rich premix burner group, and a lean premix burner group;
a gas turbine control system configured and arranged to supply each of the pilot burner group, the rich premix burner group, and the lean premix burner group with a fuel gas, the gas turbine control system comprising an analyzer input line;
a fast infrared gas analyzer configured and arranged to detect changing $C_{2+}$ of the fuel gas, the fast infrared gas analyzer having an output connected to said analyzer input line; and
a combustion pulsation monitoring and filtering system configured and arranged to monitor pulsations of said combustor,
wherein the gas turbine control system is configured to switch between a piloted fuel gas operation and a premixed fuel gas operation depending on the detected $C_{2+}$ of the fuel gas, wherein during the premixed fuel gas operation the gas turbine control system is configured to control operation of the gas turbine based on the detected $C_{2+}$ of the fuel gas determined by the fast infrared gas analyzer and the pulsations of the combustor monitored by the combustion pulsation monitoring and filtering system, and
wherein the gas turbine control system is configured to set a switch over set-point for switching over from the piloted fuel gas operation to the premixed fuel gas operation and to set a switch back set-point for switching back to the piloted fuel gas operation from the premixed fuel gas operation depending on the $C_{2+}$ of the fuel gas detected by the fast infrared gas analyzer, and the switch over set-point is a different set-point than the switch back set-point.

9. The gas turbine unit as claimed in claim 8, further comprising:
a control valve for each of said pilot burner group, said rich premix burner group, and said lean premix burner group, said control valves being in communication with said gas turbine control system via a command line.

10. The gas turbine unit as claimed in claim 8, wherein said gas turbine control system further comprises a monitoring input line, and the combustion pulsation monitoring and filtering system is connected to said gas turbine control system by said monitoring input line.

11. The gas turbine unit as claimed in claim 8, further comprising a fuel mixing device upstream of the combustor.

12. The gas turbine unit as claimed in claim 8, further comprising:
a control valve for each of said pilot burner group, said rich premix burner group, and said lean premix burner group, said control valves being in control communication with said gas turbine control system via a command line; and
the combustion pulsation monitoring and filtering system is connected to said gas turbine control system by a monitoring input line,
wherein said gas turbine control system is configured to control said control valves in accordance with measurement results of the fast infrared gas analyzer and the combustion pulsation monitoring and filtering system.

13. The gas turbine unit as claimed in claim 8, wherein said gas turbine control system optimizes a fuel distribution between the pilot burner group, the rich premix burner group, and the lean premix burner group depending on actual fuel gas composition measured by the fast infrared gas analyzer.

14. The gas turbine unit as claimed in claim 8, wherein concentrations of $CH_4$, $C_2H_6$, $C_3H_3$, and $CO_2$ are used as input for control of the gas turbine in addition to the detected $C_{2+}$.

15. The gas turbine unit as claimed in claim 8, wherein a lower heating value and a molecular weight of the fuel gas are estimated by online measuring, of $CH_4$-, $C_2H_6$-, $C_3H_8$- and $CO_2$-concentrations of the fuel gas.

16. The gas turbine unit as claimed in claim 8, wherein during the premixed fuel gas operation, fuel distribution between the rich premix burner group and the lean premix burner group is optimized depending on the detected $C_{2+}$ of the fuel gas.

17. The gas turbine unit as claimed in claim 9, further comprising a fuel mixing device upstream of the fast infrared gas analyzer and the control valves with respect to a direction of flow of the fuel gas.

\* \* \* \* \*